(12) United States Patent
Tuval et al.

(10) Patent No.: US 8,784,478 B2
(45) Date of Patent: Jul. 22, 2014

(54) TRANSAPICAL DELIVERY SYSTEM WITH VENTRUCULO-ARTERIAL OVERLFOW BYPASS

(75) Inventors: Yosi Tuval, Even Yehuda (IL); Raphael Benary, Tel Aviv (IL)

(73) Assignee: Medtronic Corevalve, Inc., Minneapolis, MN (US)

( * ) Notice: Subject to any disclaimer, the term of this patent is extended or adjusted under 35 U.S.C. 154(b) by 1497 days.

(21) Appl. No.: 12/445,824

(22) PCT Filed: Oct. 16, 2007

(86) PCT No.: PCT/IL2007/001237
§ 371 (c)(1),
(2), (4) Date: Feb. 1, 2011

(87) PCT Pub. No.: WO2008/047354
PCT Pub. Date: Apr. 24, 2008

(65) Prior Publication Data
US 2011/0112631 A1 May 12, 2011

Related U.S. Application Data (60) Provisional application No. 60/852,435, filed on Oct. 16, 2006.

(51) Int. Cl.
*A61F 2/24* (2006.01)
*A61M 1/00* (2006.01)

(52) U.S. Cl.
USPC .............................. 623/2.11; 604/4.01; 604/8

(58) Field of Classification Search
USPC ........... 623/2.11, 1.24–1.26; 604/9, 4.01, 6.1, 604/6.11, 6.16, 5.01, 8, 7
See application file for complete search history.

(56) References Cited

U.S. PATENT DOCUMENTS 3,657,744 A 4/1972 Ersek
3,671,979 A 6/1972 Moulopoulos
(Continued)

FOREIGN PATENT DOCUMENTS

CN 2007-100074433 8/2007
DE 3640745 6/1987
(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.
(Continued)

*Primary Examiner* — Corrine M McDermott
*Assistant Examiner* — Christopher L Templeton (57) ABSTRACT

Apparatus is provided for implanting a prosthetic device (108) in a patient, the apparatus includes a trocar tube (101), a first portion of which is configured to be placed in a left ventricle (12) of the patient during a procedure for implantation of the prosthetic device (108), and a second portion of which is configured to be placed in an extracardiac location during the procedure. The first portion is shaped so as to define at least one opening to an interior thereof. One or more flexible bypass tubes (103, 104, 106), each of which is coupled to the second portion, and each of which is configured to be coupled to at least one artery (20, 21, 30) of the patient, so as to create a blood flow bypass path during the procedure, from the left ventricle (12), via the opening and the bypass tubes (103, 105, 106), to the at least one artery (20, 21, 30). Other embodiments are also described.

12 Claims, 5 Drawing Sheets

(56) References Cited

U.S. PATENT DOCUMENTS

| | | | |
|---|---|---|---|
| 3,714,671 A | 2/1973 | Edwards et al. |
| 3,868,956 A | 3/1975 | Alfidi et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,612,011 A | 9/1986 | Kautzky |
| 4,647,283 A | 3/1987 | Carpentier et al. |
| 4,648,881 A | 3/1987 | Carpentier et al. |
| 4,662,885 A | 5/1987 | DiPisa, Jr. |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,085,635 A | 2/1992 | Cragg |
| 5,089,015 A | 2/1992 | Ross |
| 5,161,547 A | 11/1992 | Tower |
| 5,163,953 A | 11/1992 | Vince |
| 5,167,628 A | 12/1992 | Boyles |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,385,541 A * | 1/1995 | Kirsch et al. ................. 604/8 |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,718,725 A * | 2/1998 | Sterman et al. ............ 623/2.11 |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,861,028 A | 1/1999 | Angell |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,104 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,699 B1 | 6/2001 | Suresh et al. |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |

(56) References Cited

U.S. PATENT DOCUMENTS

| | | | |
|---|---|---|---|
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,726,648 B2 * | 4/2004 | Kaplon et al. ............... 604/9 |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,635,386 B1 | 12/2009 | Gammie |
| 7,806,919 B2 | 10/2010 | Bloom et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041864 A1 * | 11/2001 | Sweezer ............... 604/101.03 |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |

(56) References Cited

U.S. PATENT DOCUMENTS

| | | |
|---|---|---|
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0191116 A1* | 9/2004 | Jarvik et al. ............... 422/44 |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1* | 10/2005 | Bergheim ............... 606/108 |
| 2005/0240263 A1 | 10/2005 | Fogarty et al. |
| 2005/0251251 A1* | 11/2005 | Cribier ............... 623/2.11 |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0074484 A1* | 4/2006 | Huber ............... 623/2.11 |
| 2006/0089711 A1 | 4/2006 | Dolan |
| 2006/0100685 A1 | 5/2006 | Seguin et al. |
| 2006/0106415 A1* | 5/2006 | Gabbay ............... 606/198 |
| 2006/0116757 A1 | 6/2006 | Lashinski et al. |
| 2006/0135964 A1 | 6/2006 | Vesely |
| 2006/0142848 A1* | 6/2006 | Gabbay ............... 623/1.26 |
| 2006/0167468 A1* | 7/2006 | Gabbay ............... 606/108 |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0241544 A1* | 10/2006 | Haverich ............... 604/9 |
| 2006/0247570 A1* | 11/2006 | Pokorney ............... 604/9 |
| 2006/0247763 A1 | 11/2006 | Slater |
| 2006/0259134 A1 | 11/2006 | Schwammenthal et al. |

(56) References Cited

U.S. PATENT DOCUMENTS

| | | |
|---|---|---|
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0027534 A1* | 2/2007 | Bergheim et al. ............ 623/2.11 |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0112422 A1* | 5/2007 | Dehdashtian ................ 623/2.11 |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSeggesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0036479 A1 | 2/2010 | Hill et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 2 788 217 | 12/1999 |
| FR | 2815844 | 5/2000 |
| GB | 2056023 | 3/1981 |
| GB | 2398245 | 8/2004 |
| GB | 2433700 | 12/2007 |
| SU | 1271508 | 11/1986 |
| WO | 95/29640 | 11/1995 |
| WO | 00/47136 | 8/2000 |
| WO | 01/35876 | 5/2001 |
| WO | 01/49213 | 7/2001 |
| WO | 01/54625 | 8/2001 |
| WO | 01/62189 | 8/2001 |

(56) References Cited

FOREIGN PATENT DOCUMENTS

| WO | 01/64137 | 9/2001 |
|---|---|---|
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | 2006/026371 | 3/2006 |
| WO | 2008/047354 | 4/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/100198 | 8/2009 |
| WO | 2009/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. Volume II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-6.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-6.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. 1V-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal 'of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Ma, Ling, et al., "Double-crowned valved stents for off-pump mitral valve replacement," European Journal of Cardio Thoracic Surgery, 28:194-198, 2005.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Stassano et al., "Mid-term results of the valve-on-valve technique for bioprosthetic failure," Eur. J. Cardiothorac. Surg. 2000; 18:453-457.

Pavcnik et al., "Aortic and venous valve for percutaneous insertion," Min. Invas. Ther. & Allied Techol. 2000, vol. 9, pp. 287-292.

* cited by examiner

TRANSAPICAL DELIVERY SYSTEM WITH VENTRUCULO-ARTERIAL OVERLFOW BYPASS

CROSS-REFERENCES TO RELATED APPLICATIONS

This application claims priority from U.S. Provisional Patent Application 60/852,435 to Tuval et al., entitled, "Transapical delivery system with ventriculoarterial overflow bypass," filed Oct. 16, 2006, which is incorporated herein by reference.

FIELD OF THE INVENTION

The present invention relates generally to surgical instruments, in particular to instruments for performing implantation procedures on a beating heart.

BACKGROUND OF THE INVENTION

Recently, minimally invasive approaches have been developed to facilitate catheter-based implantation of valve prostheses on the beating heart, intending to obviate the need for the use of classical sternotomy and cardiopulmonary bypass. These techniques include a transapical approach for aortic valve replacement, typically involving the use of an introducer port, i.e., a large-bore overtube, of a trocar. A crimped, stented valve prosthesis reversibly coupled to a delivery catheter is transcatheterally advanced toward the native valve, where it is either forcefully deployed using a balloon catheter, or, alternatively, passively deployed using a self-expandable system.

The need to position the crimped valve at the orifice of the native aortic valve for deployment may lead to one or more of the following complications: (1) a reduction in cardiac output secondary to the obstruction of the native valve's orifice by the crimped stented valve prosthesis, until the prosthesis is fully expanded and operative; (2) a substantial increase in left ventricular afterload caused by the obstructed aortic orifice, which may result in left ventricular pump failure; and/or (3) device embolism or migration during deployment of the prosthesis, caused by a forceful left ventricular contraction against the valve prosthesis during attempted stent expansion and deployment.

Several techniques have been used to reduce the likelihood of these complications. For example, rapid right ventricular pacing induces a transient hemodynamic cardiac arrest. This technique is intended to avoid an excessive increase in afterload during the deployment of the valve prosthesis, and also to reduce the risk of device migration during deployment. However, rapid ventricular pacing deliberately causes a drop in cardiac output, albeit temporarily, which may be poorly tolerated by patients suffering from heavily hypertrophied hearts, reduced left ventricular function, and/or coronary artery disease. Alternatively, extracorporeal or intracorporeal bypass or assist devices have been used, which may further complicate the procedure significantly due to their complexity. For example, advancing part of the tubing system of the intracorporeal bypass into the pulmonary veins requires first creating a large-bore hole in the atrial septum which later needs to be closed with an occluder device. Extracorporeal bypass systems, such as ECMO (extracorporeal membrane oxygenator) may be associated with vascular, hematological and rheological complications.

U.S. Pat. No. 7,201,772 to Schwammenthal et al., which is incorporated herein by reference, describes a prosthetic device including a valve-orifice attachment member attachable to a valve in a blood vessel and including a fluid inlet, and a diverging member that extends from the fluid inlet. The diverging member includes a proximal end near the fluid inlet and a distal end distanced from the proximal end. A distal portion of the diverging member has a larger cross-sectional area for fluid flow therethrough than a proximal portion thereof. The diverging member may have a diverging taper that causes fluid to flow therethrough with pressure recovery at the distal end thereof.

PCT Publication WO 06/070372 to Schwammenthal et al., which is incorporated herein by reference, describes apparatus including a prosthetic device having a single flow field therethrough, adapted for implantation in a subject, and shaped so as to define a fluid inlet and a diverging section, distal to the fluid inlet. The prosthetic device includes a plurality of axially-extending struts which extend along at least a portion of the diverging section and diverge outwardly, such that distal ends of the struts are spaced further from one another than proximal ends of the struts throughout a cardiac cycle of the subject. The diverging section includes a diverging envelope coupled to the struts, which is adapted to assume an open position thereof during systole, permitting blood flow through the device, and which is adapted to collapse to a closed position thereof during diastole, inhibiting blood flow through the device.

PCT Publication WO 05/002466 to Schwammenthal et al., which is incorporated herein by reference, describes prosthetic devices as described for use in the treatment of aortic stenosis in the aortic valve of a patient's heart. The prosthetic device has a compressed state for transarterial delivery, and is expandable to an expanded state for implantation. The prosthetic device includes an expandable metal base constructed so as to be implantable in the expanded state of the prosthetic device in the aortic annulus of the aortic valve; and an inner envelope lining tune inner surface of the metal base. The inner envelope, in the expanded state of the prosthetic device, extends into the aorta and is of a diverging conical configuration, in which its diameter gradually increases from its proximal end within the aortic annulus to its distal end extending into the aorta, such as to produce, during systole, a non-turbulent blood flow into the aorta with pressure recovery at the distal end of the inner envelope. Preferably, the distal end includes a prosthetic valve which is also concurrently implanted, but such a prosthetic valve may be implanted separately in the aorta. Also described are preferred methods of implanting such prosthetic devices.

The following patents, all of which are incorporated herein by reference, may be of interest:
U.S. Pat. No. 6,395,026 to Aboul-Hosn et al.
U.S. Pat. No. 6,935,344 to Aboul-Hosn et al.
U.S. Pat. No. 6,532,964 to Aboul-Hosn et al.

SUMMARY OF THE INVENTION

In some embodiments of the present invention, a delivery system housing a valvular prosthetic device is configured to allow blood to bypass the aortic valve during the advancement of the delivery system through the aortic valve. Typically, the system comprises a delivery catheter, e.g., a trocar tube, which houses the prosthesis in a compressed state at a distal end of the tube. The trocar tube is typically transapically advanced into the heart of the patient. In some embodiments, however, the trocar tube is configured for transmyocardial advancement at locations other than the apex of the heart. For example, the trocar tube may be introduced anterior and superior to the apex of the heart at the left ventricle. During delivery of the prosthesis to the aortic surface of the native aortic valve, a distal portion of the trocar tube is advanced through the aortic valve, thereby creating a temporary blockage at the aortic valve.

Typically, a ventricular portion of the tube is shaped to provide a plurality of holes configured to drain the blood from the left ventricle. In order to bypass the temporary blockage at the aortic valve, the trocar tube is configured to direct blood flow from the left ventricle to one or more arteries downstream of the aorta (e.g., the femoral arteries, the common iliac arteries, or the descending aorta) rather than through the aortic valve. The bypass (a) helps maintain normal cardiac output (or prevent a critical drop in output), and (b) helps reduce the possibility of an excessive increase in contractile resistance of the left ventricle against pressure generated by the blockage.

Typically, an extracardiac portion of the tube is shaped to provide at least one port which is coupled to a bypass tube at a first end thereof. The second end of the bypass tube is configured to be disposed within one of the abovementioned arteries. The bypass tube is configured to direct blood from the left ventricle into the artery. The bypass tube typically comprises a mechanical valve mechanism that facilitates unidirectional blood flow from the left ventricle to the arteries. Thus; when a prosthetic device is inserted into the aorta, the system creates a bypass flow pathway from the left ventricle into the downstream arteries by bypassing the temporary blockage of the aortic valve created by the trocar tube.

In some embodiments of the present invention, the distal end of the trocar tube remains within the left ventricle and is not advanced through the native aortic valve. In such an embodiment, the prosthetic device is typically surrounded by a sheath which prevents expansion of the compressed prosthesis during the advancement of the prosthesis through the valve. The sheath is removed once the prosthesis is advanced through the valve, allowing the prosthesis to expand. Alternatively, the prosthesis is not self-expandable, and is instead expanded by inflating a balloon disposed within the prosthesis. Since the distal end of the trocar tube remains disposed within the left ventricle in this embodiment, the blood is allowed to flow through the trocar tube from the left ventricle to one or more extracardiac arterial sites that are downstream of the left ventricle. In such an embodiment, the trocar tube typically (but not necessarily) does not provide the plurality of holes described hereinabove.

In an embodiment of the present invention, a transmyocardial approach is used in order to introduce a cardiopulmonary bypass system into the right ventricle of the patient. In another embodiment of the present invention, the cardiopulmonary bypass system is introduced through the right ventricular apex. In either embodiment, the cardiopulmonary bypass system comprises a delivery catheter, e.g., a trocar tube (as described hereinabove), which houses a prosthesis configured to be advanced through the native pulmonary valve. As the device is positioned in the vicinity of the pulmonary valve, the delivery catheter creates a temporary blockage at the pulmonary valve. Sheaths coupled to extracardiac portions of the trocar tube direct blood from the right ventricle to the pulmonary arteries at a site downstream of the pulmonary valve, in a manner as described hereinabove with respect to the aortic valve bypass system.

In embodiments in which a system as described is advanced either into the left ventricle or into the right ventricle, the system is configured to passively induce blood flow through the trocar tube in response to the natural pressure force exerted on the blood by the ventricular contractile force.

In other embodiments, the system is coupled to an active assist pump (e.g., a roller pump), in order to direct the blood flow through the trocar tube. For embodiments in which the pump is used, the system may also serve as a left ventricular assist device (LVAD) in acute left ventricular failure patients, particularly when combined with the transmyocardial and/or transapical approach to insert the system into the patient's heart. For some applications, the delivery system is configured to provide another ventriculoarterial bypass, such as ventriculo-brachial or ventriculoaortic bypass.

There is therefore provided, in accordance with an embodiment of the present invention, apparatus for implanting a prosthetic device in a patient, the apparatus including:
- a trocar tube,
  - a first portion of which is configured to be placed in a left ventricle of the patient during a procedure for implantation of the prosthetic device, and
  - a second portion of which is configured to be placed in an extracardiac location during the procedure, the first portion being shaped so as to define at least one opening to an interior thereof; and
- one or more flexible bypass tubes, each of which is coupled to the second portion, and each of which is configured to be coupled to at least one artery of the patient, so as to create a blood flow bypass path during the procedure, from the left ventricle, via the opening and the bypass tubes, to the at least one artery.

In an embodiment, the apparatus includes one or more unidirectional valves configured to prevent backflow of blood into the left ventricle.

In an embodiment, a distal end of the first portion is shaped so as to define the at least one opening therethrough to the interior of the first portion, and the trocar tube is configured to enable introduction of the prosthetic device via the at least one opening.

In an embodiment, the apparatus is configured to allow for passive blood flow through the at least one opening of the trocar tube in response to force generated by the left ventricle.

In an embodiment, the apparatus includes an external source of power, the source of power is configured to facilitate active blood flow through the at least one opening of the trocar tube.

In an embodiment, the trocar tube is configured for transmyocardial delivery through a free wall of a heart of the patient.

In an embodiment, the trocar tube is configured for transapical delivery through an apex of a heart of the patient, into the left ventricle of the patient.

In an embodiment, the valve includes an aortic valve, and the one or more bypass tubes are configured to create a blood flow bypass to a descending aorta of the patient.

In an embodiment, the valve includes an aortic valve, and the one or more bypass tubes are configured to create a blood flow bypass to a femoral artery of the patient.

In an embodiment, the valve includes an aortic valve, and the one or more bypass tubes are configured to create a blood flow bypass to an iliac artery of the patient.

In an embodiment, the first portion is shaped to define a wall, the wall being shaped so as to define the at least one opening to the interior of the first portion.

In an embodiment, the wall of the first portion is shaped to provide a plurality of openings.

In an embodiment, the first portion of the trocar tube is configured to house therein the prosthetic device in a compressed state thereof.

In an embodiment, the prosthetic device is configured to be pushed through a valve of the patient from within the first portion.

In an embodiment, the prosthetic device is configured to expand from the compressed state once the prosthetic device is pushed through the valve.

In an embodiment, a portion of the first portion is configured to be advanced through a valve of the subject, and the prosthetic device is configured to be pushed from within the first portion once the first portion is advanced through the valve.

In an embodiment, the prosthetic device is configured to expand from the compressed state once the prosthetic device is pushed from within the first portion of the tube.

In an embodiment, the prosthetic device includes a prosthetic valve.

In an embodiment, the prosthetic valve is configured to be advanced through a native valve of the patient.

In an embodiment, the one or more bypass tubes are configured to create the blood flow bypass path during advancement of the prosthetic valve through the native valve of the patient.

There is further provided, in accordance with an embodiment of the present invention, a method for implanting a prosthetic device in a patient, the method including:
transmyocardially advancing a trocar tube housing a prosthesis into a left ventricle of a subject;
advancing the prosthesis through a valve of the patient; and
during the advancing of the prosthesis, providing a blood flow bypass path from the left ventricle of the patient, through at least a portion of the trocar tube, and to an extracardiac arterial site downstream from the valve.

In an embodiment, advancing the prosthesis includes pushing a distal end of the trocar tube through the valve of the patient.

In an embodiment, the method includes allowing the prosthesis to expand following the advancing of the prosthesis through the valve.

In an embodiment, the valve includes an aortic valve, advancing the prosthesis through the valve includes advancing the prosthesis through the aortic valve, and providing the blood flow bypass path includes providing the blood flow bypass path from the left ventricle to a descending aorta of the patient.

In an embodiment, the valve includes an aortic valve, advancing the prosthesis through the valve includes advancing the prosthesis through the aortic valve, and providing the blood flow bypass path includes providing the blood flow bypass path from the left ventricle to a femoral artery of the patient.

In an embodiment, the valve includes an aortic valve, advancing the prosthesis through the valve includes advancing the prosthesis through the aortic valve, and providing the blood flow bypass path includes providing the blood flow bypass path from the left ventricle to an iliac artery of the patient.

In an embodiment, the method includes restricting blood flow through the valve during the advancing of the prosthesis therethrough.

In an embodiment, providing a blood flow bypass path includes draining blood from the left ventricle to the extracardiac site in response to the restricting.

In an embodiment, draining the blood includes actively draining the blood.

In an embodiment, restricting the blood flow includes increasing a contractile force of the left ventricle, and draining the blood includes allowing the blood to be passively drained through the trocar tube in response to the increasing.

There is yet further provided, in accordance with an embodiment of the present invention, apparatus for implanting a prosthetic device in a patient, the apparatus including:
a trocar tube,
a first portion of which is configured to be placed in a right ventricle of the patient during a procedure for implantation of the prosthetic device, and
a second portion of which is configured to be placed in an extracardiac location during the procedure, the first portion being shaped so as to define at least one opening to an interior thereof; and
one or more flexible bypass tubes, each of which is coupled to the second portion, and each of which is configured to be coupled to at least one artery of the patient, so as to create a blood flow bypass path during the procedure, from the right ventricle, via the opening and the bypass tubes, to the at least one artery.

In an embodiment, the apparatus includes one or more unidirectional valves configured to prevent backflow of blood into the right ventricle.

In an embodiment, a distal end of the first portion is shaped so as to define the at least one opening therethrough to the interior of the first portion, and the trocar tube is configured to enable introduction of the prosthetic device via the at least one opening.

In an embodiment, the apparatus is configured to allow for passive blood flow through the at least one opening of the trocar tube in response to force generated by the right ventricle.

In an embodiment, the apparatus includes an external source of power, the source of power is configured to facilitate active blood flow through the at least one opening of the trocar tube.

In an embodiment, the trocar tube is configured for transmyocardial delivery through a free wall of a heart of the patient.

In an embodiment, the trocar tube is configured for transapical delivery through a right ventricular apex of a heart of the patient, into the right ventricle of the patient.

In an embodiment, the valve includes a pulmonary valve, and the one or more bypass tubes are configured to create a blood flow bypass to a pulmonary artery of the patient.

In an embodiment, the first portion is shaped to define a wall, the wall being shaped so as to define the at least one opening to the interior of the first portion.

In an embodiment, the wall of the first portion is shaped to provide a plurality of openings.

In an embodiment, the first portion of the trocar tube is configured to house therein the prosthetic device in a compressed state thereof.

In an embodiment, the prosthetic device is configured to be pushed through a valve of the patient from within the first portion.

In an embodiment, the prosthetic device is configured to expand from the compressed state once the prosthetic device is pushed through the valve.

In an embodiment, a portion of the first portion is configured to be advanced through a valve of the subject, and the prosthetic device is configured to be pushed from within the first portion once the first portion is advanced through the valve.

In an embodiment, the prosthetic device is configured to expand from the compressed state once the prosthetic device is pushed from within the first portion of the tube.

In an embodiment, the prosthetic device includes a prosthetic valve.

In an embodiment, the prosthetic valve is configured to be advanced through a native valve of the patient.

In an embodiment, the one or more bypass tubes are configured to create the blood flow bypass path during advancement of the prosthetic valve through the native valve of the patient.

There is additionally provided, in accordance with an embodiment of the present invention, a method for implanting a prosthetic device in a patient, the method including:

transmyocardially advancing a trocar tube housing a prosthesis into a right ventricle of a patient;

advancing the prosthesis through a valve of the patient; and during the advancing of the prosthesis, providing a blood flow bypass path from the right ventricle of the patient, through at least a portion of the trocar tube, and to an extracardiac arterial site downstream from the valve.

In an embodiment, transmyocardially advancing the trocar tube includes transmyocardially advancing the trocar tube through a free wall of the heat.

In an embodiment, transmyocardially advancing the trocar tube includes transapically advancing the tube through a right ventricular apex and into the right ventricle of the patient.

In an embodiment, advancing the prosthesis includes pushing a distal end of the trocar tube through the valve of the patient.

In an embodiment, the method includes allowing the prosthesis to expand following the advancing of the prosthesis through the valve.

In an embodiment, the valve includes a pulmonary valve, advancing the prosthesis through the valve includes advancing the prosthesis through the pulmonary valve, and providing the blood flow bypass path includes providing the blood flow bypass path from the right ventricle to a pulmonary artery of the patient.

In an embodiment, the method includes restricting blood flow through the valve during the advancing of the prosthesis therethrough.

In an embodiment, providing a blood flow bypass path includes draining blood from the right ventricle to the extracardiac site in response to the restricting.

In an embodiment, draining the blood includes actively draining the blood.

In an embodiment, restricting the blood flow includes increasing a contractile force of the right ventricle, and draining the blood includes allowing the blood to be passively drained through the trocar tube in response to the increasing.

There is also provided, in accordance with an embodiment of the present invention, apparatus for implanting a prosthetic device in a patient, the apparatus including:

a trocar tube, a first portion of which is configured to be placed in a left ventricle of the patient during a procedure for implantation of the prosthetic device, and a second portion of which is configured to be placed in an extracardiac location during the procedure, wherein the first portion is shaped so as to define at least one opening to an interior thereof; and, one or more flexible bypass tubes, each of which is coupled to the second portion, and each of which is configured to be coupled to at least one artery of the patient, so as to create a blood flow bypass path during the procedure, from the left ventricle, via the opening and the bypass tubes, to the at least one artery.

In an embodiment, the apparatus includes one or more one-way valves configured to prevent backflow of blood into the left ventricle.

For some applications, a wall of the first portion of the trocar is shaped so as to define the at least one opening therethrough to the interior of the first portion.

Alternatively, a distal end of the first portion is shaped so as to define the at least one opening therethrough to the interior of the first portion, and the trocar tube is configured enable introduction of the prosthetic device via the at least one opening.

For some applications, the apparatus is configured such that blood flow through the bypass is driven only by force generated by the left ventricle. Alternatively, the apparatus is configured such that blood flow through the bypass is at least in part driven by an external source of power.

The present invention will be more fully understood from the following detailed description of embodiments thereof, taken together with the drawings, in which:

DETAILED DESCRIPTION OF EMBODIMENTS

Figure 1:
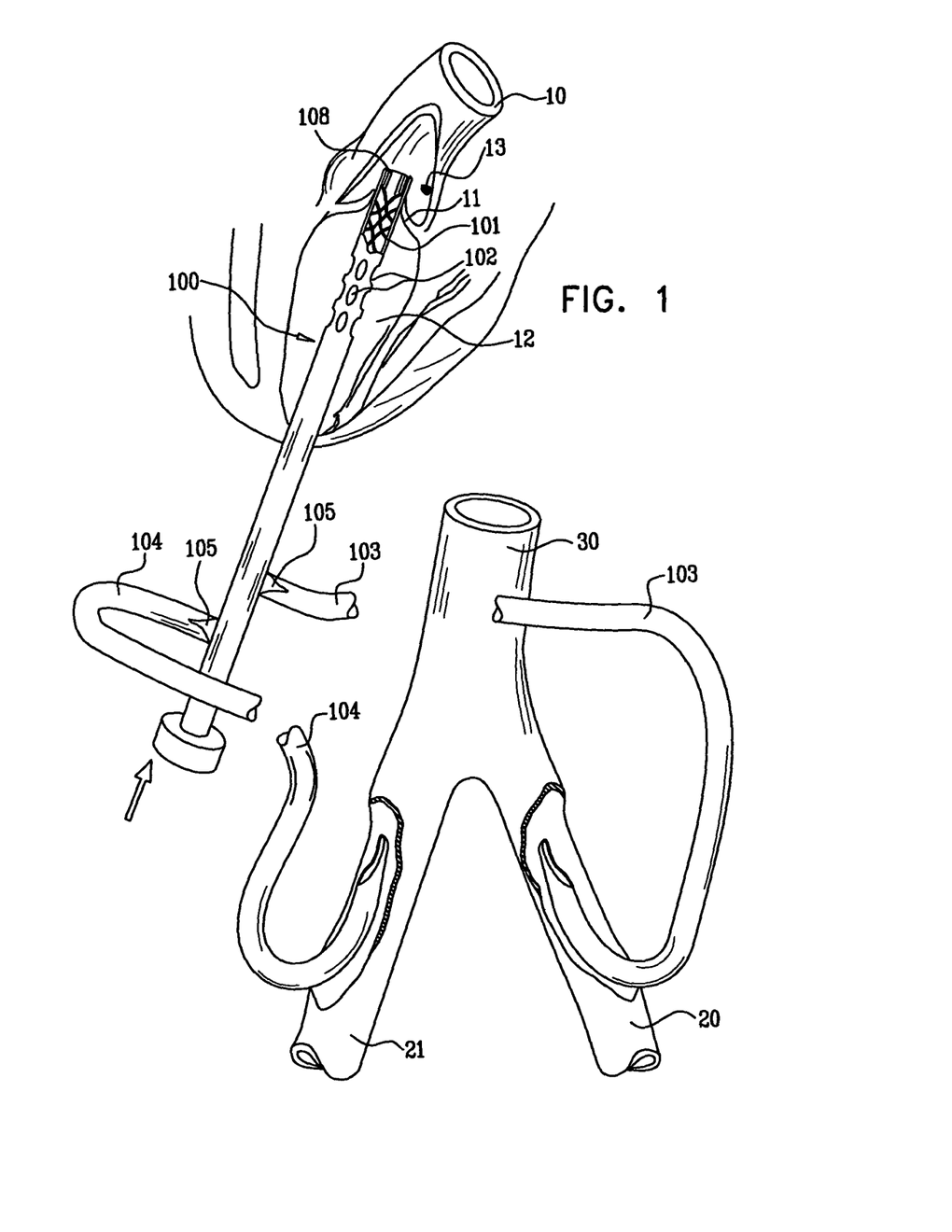
FIG. 1 is a schematic illustration of a bypass device and delivery system therefor, in accordance with an embodiment of the present invention.

FIG. 1 is a schematic illustration of a prosthetic device delivery system 100, in accordance with an embodiment of the present invention. Delivery system 100 comprises a trocar tube 101 housing a prosthetic valvular device 108 at a distal end of tube 101. Typically, prosthetic device 108 comprises a self-expanding, biocompatible, resilient material, e.g., nitinol, stainless steel, or other such materials known in the art. The distal end of trocar tube 101 is configured to be advanced toward leaflets 11 of a native aortic valve of the patient. In some embodiments, the distal end of tube 101 is configured to be advanced through leaflets 11 to a site within the ascending aorta 10, downstream of leaflets 11. During advancement of prosthetic device 108 through leaflets 11, system 100 creates a temporary blockage at the aortic valve. In order to supply blood to arteries downstream of the heart during the advancement and subsequent implantation of prosthetic device 108, system 100 provides a bypass mechanism configured to supply blood from left ventricle 12 to one or more arteries 30 downstream of aorta 10.

Trocar tube 101 is shaped so as to define a plurality of holes 102 at a ventricular portion of tube 101. The ventricular portion of tube 101 is configured to be disposed in left ventricle 12 as prosthetic device 108 is delivered to the aortic surface of leaflets 11. Typically, prosthetic device 108 is advanced through the aortic valve as the heart is beating. The distal end of tube 101 occludes the aortic valve during the delivery of device 108 therethrough. The blockage, in combination with contractile force of left ventricle 12 against the occluded valve, forces the blood to passively flow from ventricle 12 into holes 102 of tube 101.

Delivery system 100 further comprises one or more flexible bypass tubes 103 and 104, which are coupled to an extracardiac portion of trocar tube 101. Typically, tubes 103 and 104 comprise a flexible material, e.g., silicone, rubber, or polyvinyl chloride (PVC). First ends of tubes 103 and 104 are coupled to extracardiac portions of tube 101, as shown, via holes in the extracardiac portions of tube 101. During the percutaneous delivery of system 100, portions of bypass tubes 103 and 104 remain disposed outside the body of the patient, while the first ends of tubes 103 and 104 are advanced toward the heart along with the advancement of system 100. Once the intracardiac portion of system 100 is positioned in left ventricle 12 of the heart, second ends of tubes 103 and 104 are introduced within artery 30 of the patient, typically via percutaneous incisions in the vicinity of artery 30. As shown, tube 103 is placed in a first branch 20 of artery 30, while tube 104 is placed in a second branch 21 of artery 30. In some embodiments of the present invention, artery 30 includes a femoral artery. In some embodiments, artery 30 includes an iliac artery. In some embodiments, artery 30 includes a descending aorta, as shown hereinbelow with reference to FIG. 4.

Typically, bypass tubes 103 and 104 comprise one or more unidirectional valves 105 that prevent retrograde flow of blood into left ventricle 12. In some embodiments, trocar tube 101 comprises at least one valve 105.

During the advancement and subsequent implantation of prosthetic device 108 at the aortic valve, holes 102 drain blood from ventricle 12 during contraction thereof. System 100 thereby facilitates a bypass flow of the blood from ventricle 12, into tube 101, through bypass tubes 103 and 104, and ultimately into downstream artery 30. In such an embodiment, blood is generally not passed directly through the aortic valve and into aorta 10.

It is to be noted that the use of two bypass tubes 103 and 104 is shown by way of illustration and not limitation, and that one or more bypass tubes may be used.

Figure 3:
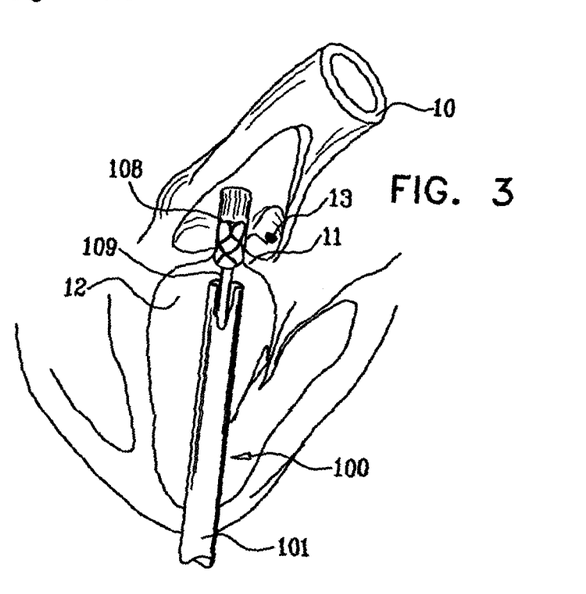
FIG. 3 is a schematic illustration of a prosthesis emerging from within the trocar tube of FIG. 2, in accordance with an embodiment of the present invention.

Once the distal end of tube 101 is advanced through leaflets 11, prosthetic device 108 is pushed from within tube 101 by a prosthetic device delivery shaft 109 (FIG. 3).

It is to be noted that although blood is directed away from aorta 10 during systole, coronary ostia 13 are still supplied blood during retroperfusion of the blood within the arteries during the cardiac cycle.

Figure 2:
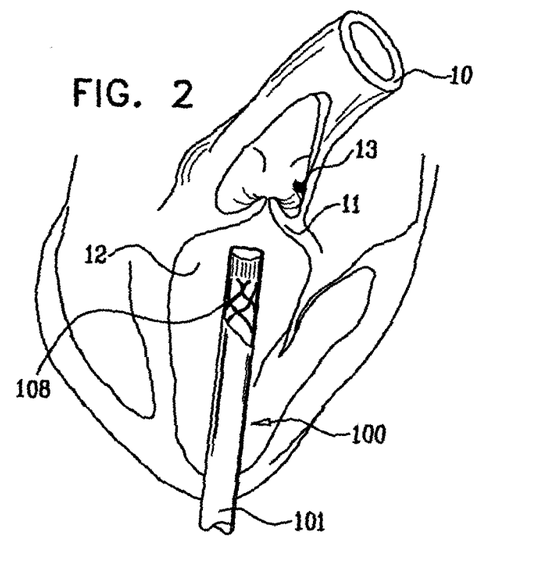
FIG. 2 is a schematic illustration of a trocar tube of the delivery system of FIG. 1, within a left ventricle of a patient, in accordance with an embodiment of the present invention.

FIG. 2 is a schematic illustration of the distal end of trocar tube 101 being placed within left ventricle 12 of the patient, in accordance with an embodiment of the present invention. During advancement of system 100 toward the aortic valve, prosthetic device 108 is disposed in a compressed state within trocar tube 101.

FIG. 3 is a schematic illustration of the advancement of prosthetic device 108 through leaflets 11 of the aortic valve, in accordance with an embodiment of the present invention. As shown, the distal end of trocar tube 101 is configured to remain upstream of valve leaflets 11 in a ventricular vicinity of leaflets 11. In some embodiments, the distal end of tube 101 may be advanced at least in part, but typically not fully, through the native valve.

During advancement of prosthetic device 108 and prosthetic device delivery shaft 109 toward the aortic valve, the presence of device 108 within the distal end of tube 101 restricts drainage of blood from the left ventricle into tube 101. Once the distal end of tube 101 reaches the ventricular surface of the aortic valve, prosthetic device 108 is pushed from within tube 101 by pushing on the prosthesis delivery shaft 109. Pushing prosthesis 108 from within tube 101 frees an opening at the distal end of tube 101, thereby allowing blood from ventricle 12 to drain into the interior of tube 101. (Alternatively or additionally, holes 102 allow such drainage of blood.)

Prosthetic device 108 is further advanced through the aortic valve and is allowed to self-expand once inside aorta 10. In some embodiments, a balloon is disposed within the compressed prosthesis during the advancement of prosthetic device 108 toward the aortic valve of the patient. Once prosthetic device 108 is positioned at the aortic surface of the aortic valve, prosthetic device 108 is made to expand by inflating the balloon.

As shown, the distal end of trocar tube 101 is typically not advanced through the native valve. Instead, once prosthetic device 108 is advanced through native aortic valve leaflets 11, blood is allowed to passively flow around the prosthetic device shaft 109, and into an opening at the distal end of trocar tube 101. In such an embodiment, trocar tube 101 is not shaped so as to define holes 102, as described hereinabove with reference to FIGS. 1 and 2. However, in some embodiments, trocar tube 101 is shaped so as to define holes 102. In such an embodiment, blood flows through holes 102 as well as through the opening at the distal end of tube 101.

As described hereinabove with reference to FIG. 1, system 100 bypasses blood from left ventricle 12 to any suitable downstream artery 30.

Figure 4:
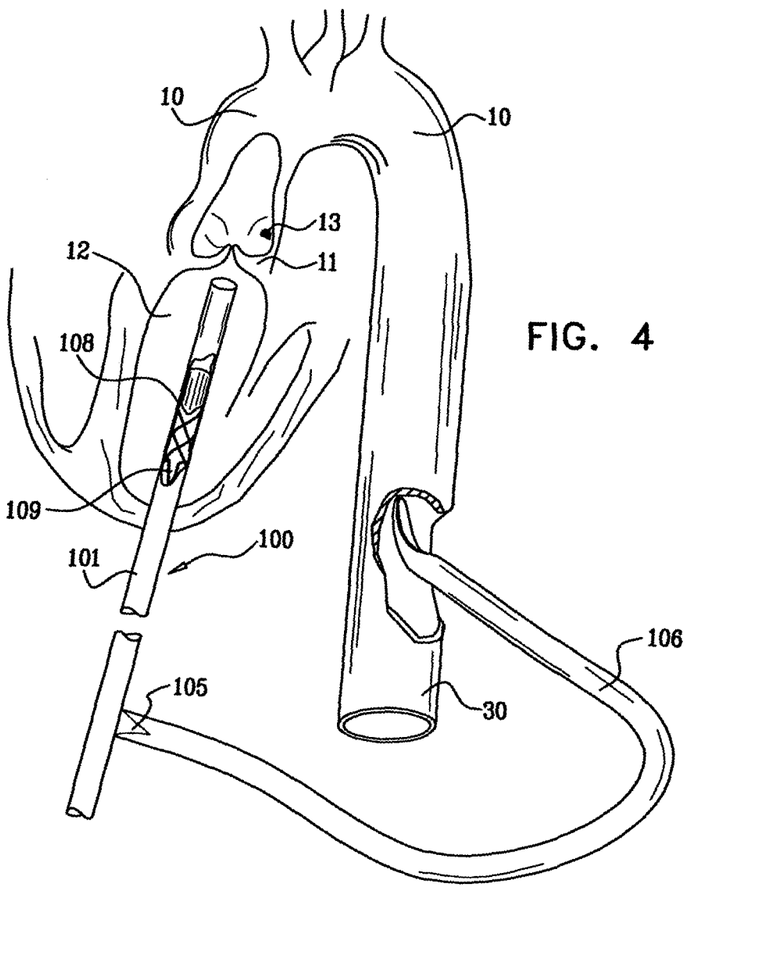
FIG. 4 is a schematic illustration of a portion of the bypass device within a descending aorta of the patient, in accordance with an embodiment of the present invention.

FIG. 4 is a schematic illustration of the bypass blood flow from left ventricle 12 to one or more extracardiac sites that are downstream of left ventricle 12, as described hereinabove with reference to FIGS. 1-3, with the exception that a portion of system 100 is inserted into the descending aorta of the patient, in accordance with an embodiment of the present invention. As shown, blood travels unidirectionally from within tube 101 and into a bypass tube 106 via valve 105. Bypass tube 106 diverts the blood from ventricle 12 into downstream artery 30, the descending aorta (as shown). Bypass tube 106 is inserted into the body of the patient as described hereinabove with reference to tubes 103 and 104, with the exception that the second end of bypass tube 106 is inserted, via a percutaneous incision, into the descending aorta.

Figure 5:
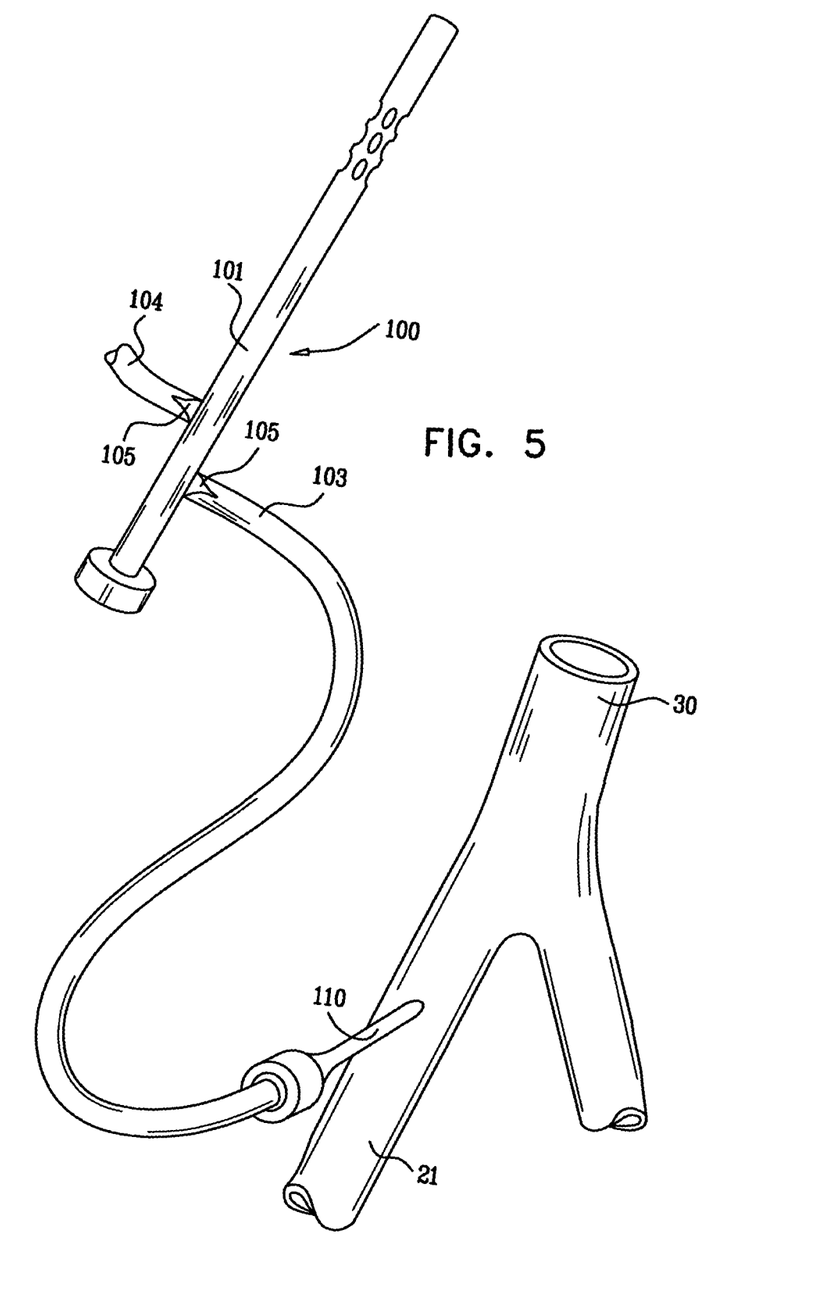
FIG. 5 is a schematic illustration of a portion of the bypass device inserted into a downstream artery of the aorta, in accordance with an embodiment of the present invention.

FIG. 5 is a schematic illustration of system 100 described hereinabove with reference to FIG. 1, with the exception that system 100 comprises an arterial introducer sheath 110, in accordance with an embodiment of the present invention. The second end of bypass tube 103 is inserted into downstream artery 30 via arterial introducer sheath 110. Sheath 110 is configured to generate a smooth flow of blood from within bypass tube 103 into artery 30. For clarity of illustration, the continuation of bypass tube 104 is not shown. It is to be noted that arterial sheath 110 may be used in combination with any of the tubes described herein.

Figure 6:
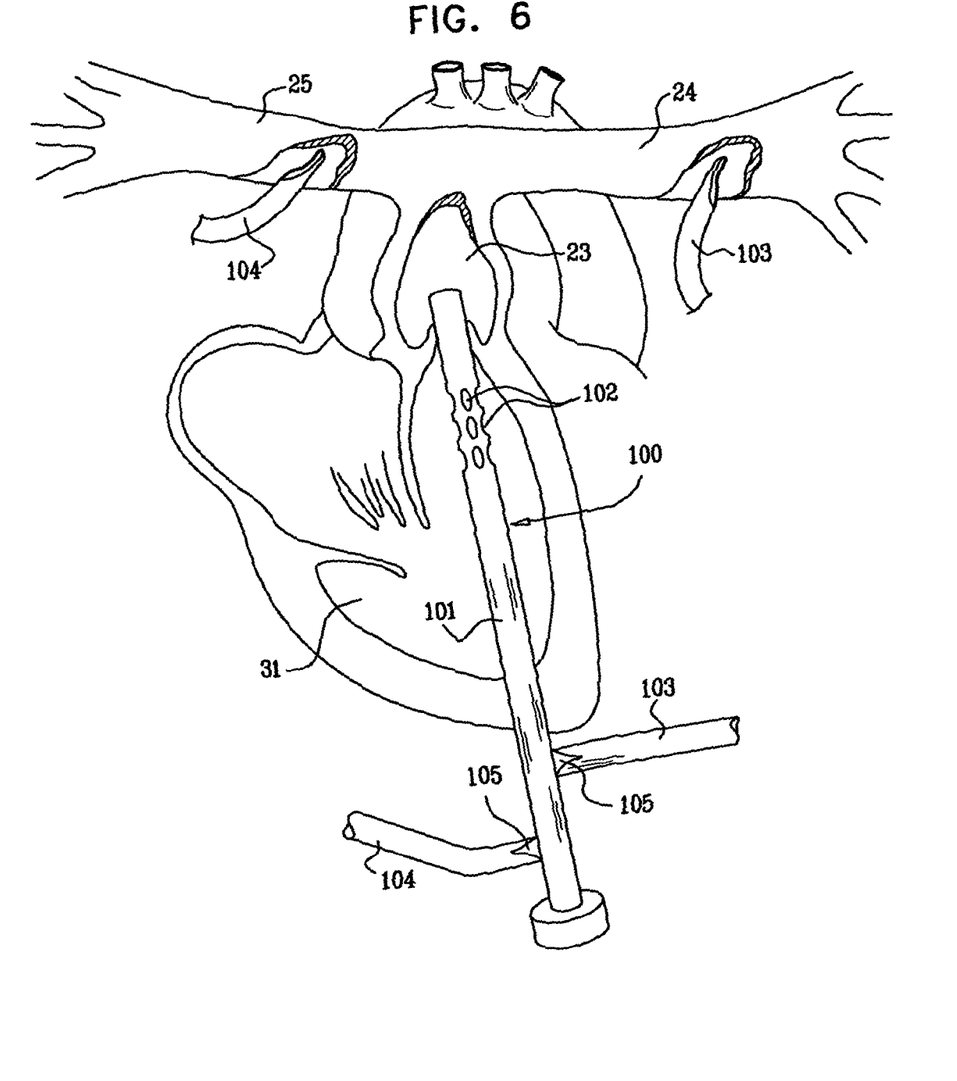
FIG. 6 is a schematic illustration of a bypass device and delivery system therefor, in accordance with another embodiment of the present invention.

Reference is now made to FIG. 6, which is a schematic illustration of system 100 comprising a cardiopulmonary bypass system, in accordance with an embodiment of the present invention. Typically, trocar tube 101 is advanced into a right ventricle 31 using a transmyocardial approach, whereby tube 101 is advanced through the right ventricular apex of the heart. In some embodiments, tube 101 is advanced through any portion of the free wall of the heart using a transmyocardial approach (embodiment not shown).

Once the distal end of tube 101 is advanced through the pulmonary valve, blood is drained through holes 102 of tube 101, through tube 101, and subsequently into bypass tubes 103 and 104. The distal end of tube 101 occludes the pulmonary valve as it is advanced through the pulmonary valve. The blockage, in combination with contractile force of right ventricle 31 on the blood, forces the blood to passively flow from ventricle 31 into holes 102 of tube 101. In a manner as described hereinabove with reference to FIG. 1, a second end of tube 103 is disposed within a left branch 24 of pulmonary artery 23, and a second end of tube 104 is disposed within a right branch 25 of pulmonary artery 23. Such a configuration diverts blood from ventricle 31 and into branches 24 and 25 of pulmonary artery 23.

It is to be noted that system 100 shown in FIG. 6 without prosthetic device 108 is shown by way of illustration and not limitation, and that the distal end of tube 101 typically houses device 108.

It is to be further noted that the cardiopulmonary bypass system described with reference to FIG. 6 may be used independently of or in combination with techniques and apparatus described hereinabove with reference to FIGS. 1-5. For example, the distal end of tube 101 is configured to remain within right ventricle 31 while not being advanced through the pulmonary valve, as described hereinabove with reference to FIG. 3. In such an embodiment, blood is drained from ventricle 31 into tube 101 through the opening at the distal end of tube 101.

In either embodiment in which tube 101 is advanced into either left ventricle 12 or right ventricle 31, blood is caused to passively flow through trocar 101 tube in response to the natural pressure force exerted on the blood by the ventricular contractile force. Alternatively, in some embodiments, system 100 is coupled to an active assist pump (e.g., a roller pump) in order to direct the blood flow through trocar tube 101.

The scope of the present invention includes embodiments described in the following patent and patent applications, which are assigned to the assignee of the present application and are incorporated herein by reference. In an embodiment, techniques and apparatus described in one or more of the following patent and patent applications are combined with techniques and apparatus described herein:

U.S. Pat. No. 7,201,772, filed Dec. 30, 2004;
International Patent Application PCT/IL2005/01399, filed Dec. 29, 2005;
International Patent Application PCT/IL2004/000601, filed Jul. 6, 2004, and U.S. patent application Ser. No. 10/563,384, filed Jan. 5, 2006 in the national stage thereof; and/or
U.S. patent application Ser. No. 11/728,253, filed Mar. 23, 2007, entitled, "Valve prosthesis fixation techniques using sandwiching."

Each of these patent and patent applications are incorporated herein by reference.

For some applications, techniques described herein are practiced in combination with techniques described in one or more of the references cited in the Cross-references section or Background section of the present patent application, which are incorporated herein by reference.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for implanting a prosthetic device in a patient, the method comprising:
    transmyocardially advancing a trocar tube housing a prosthesis into a left ventricle of a subject, wherein the prosthesis restricts drainage of blood from the left ventricle into an opening at a distal end of the trocar tube when the prosthesis is housed in the trocar tube;
    advancing the prosthesis through a valve of the patient, wherein advancing the prosthesis frees the opening in the distal end of tube, thereby allowing blood from the left ventricle to drain into an interior of the trocar tube; and
    during the advancing of the prosthesis, providing a blood flow bypass path from the left ventricle of the patient, into the opening at the distal end of the trocar tube, through at least a portion of the interior of the trocar tube, and to an extracardiac arterial site downstream from the valve.

2. The method according to claim 1, wherein transmyocardially advancing the trocar tube comprises transmyocardially advancing the trocar tube through a free wall of the heart.

3. The method according to claim 1, wherein transmyocardially advancing the trocar tube comprises transapically advancing the tube into the left ventricle of the patient.

4. The method according to claim 1, wherein advancing the prosthesis comprises pushing a distal end of the trocar tube through the valve of the patient.

5. The method according to claim 1, further comprising allowing the prosthesis to expand following the advancing of the prosthesis through the valve.

6. The method according to claim 1, wherein the valve includes an aortic valve, wherein advancing the prosthesis through the valve comprises advancing the prosthesis through the aortic valve, and wherein providing the blood flow bypass path comprises providing the blood flow bypass path from the left ventricle to a descending aorta of the patient.

7. The method according to claim 1, wherein the valve includes an aortic valve, wherein advancing the prosthesis through the valve comprises advancing the prosthesis through the aortic valve, and wherein providing the blood flow bypass path comprises providing the blood flow bypass path from the left ventricle to a femoral artery of the patient.

8. The method according to claim 1, wherein the valve includes an aortic valve, wherein advancing the prosthesis through the valve comprises advancing the prosthesis through the aortic valve, and wherein providing the blood flow bypass path comprises providing the blood flow bypass path from the left ventricle to an iliac artery of the patient.

9. The method according to any one of claims 1-8, further comprising restricting blood flow through the valve during the advancing of the prosthesis therethrough.

10. The method according to claim 9, wherein providing a blood flow bypass path comprises draining blood from the left ventricle to the extracardiac site in response to the restricting.

11. The method according to claim 10, wherein draining the blood comprises actively draining the blood.

12. The method according to claim 10, wherein restricting the blood flow comprises increasing a contractile force of the left ventricle, and wherein draining the blood comprises allowing the blood to be passively drained through the trocar tube in response to the increasing.

* * * * *